US007416863B2

(12) United States Patent
Moeckel et al.

(10) Patent No.: US 7,416,863 B2
(45) Date of Patent: *Aug. 26, 2008

(54) NUCLEOTIDE SEQUENCES FOR ENCODING OF THE LYSR2-GENE

(75) Inventors: Bettina Moeckel, Duesseldorf (DE);
Mike Farwick, Bielefeld (DE); Thomas Hermann, Bielefeld (DE); Caroline Kreutzer, Melle (DE); Walter Pfefferle, Halle (DE)

(73) Assignee: Degussa AG, Duesseldorf (DE)

( * ) Notice: Subject to any disclaimer, the term of this patent is extended or adjusted under 35 U.S.C. 154(b) by 451 days.

This patent is subject to a terminal disclaimer.

(21) Appl. No.: 11/178,485

(22) Filed: Jul. 12, 2005

(65) Prior Publication Data

US 2005/0282259 A1 Dec. 22, 2005

Related U.S. Application Data

(62) Division of application No. 09/826,909, filed on Apr. 6, 2001, now Pat. No. 7,078,502.

(30) Foreign Application Priority Data

Aug. 10, 2000 (DE) .................................. 100 39 047
Mar. 3, 2001 (DE) .................................. 101 10 346

(51) Int. Cl.
*C12P 19/34* (2006.01)
(52) U.S. Cl. ................. 435/91.2; 536/24.32; 536/24.33
(58) Field of Classification Search ........................ None
See application file for complete search history.

(56) References Cited

U.S. PATENT DOCUMENTS 7,078,502 B2 * 7/2006 Moeckel et al. ............. 536/23.1

FOREIGN PATENT DOCUMENTS

EP 1 108 790 6/2001

WO WO 01/00804 1/2001

OTHER PUBLICATIONS

Josef Cremer, et al., Applied and Environmental Microbiology, vol. 57, pp. 1746-1752 "Control of the Lysine Biosynthesis Sequence in *Corynebacterium Glutamicum* as Analyzed by Overexpression of the Individual Corresponding Genes", Jun. 1991.
L. Eggeling, et al., Appl Microbiol Biotechnol, vol. 49, pp. 24-30, "Improved L-Lysine Yield With *Corynebacterium Glutamicum*: Use of *Dapa* Resulting in Increased Flux Combined With Growth Limitation", 1998.
Bernhard J. Eikmanns, et al., Antonie van Leeuwenhock, vol. 64, pp. 145-163, "Molecular Aspects of Lysine, Threonine, and Isoleucine Biosynthesis in *Corynebacterium Glutamicum*", 1993.
C. Fernéndez-González, et al., Appl Microbiol Biotechnol, vol. 46, pp. 554-558, "Construction of L-Lysine-Overproducing Strains of *Brevibacterium Lactofermentum* by Targeted Disruption of the *HOM* and *THRB* Genes", 1996.
Reinhard Kraemer, Journal of Biotechnology, vol. 45, pp. 1-21, "Genetic and Physiological Approaches for the Production of Amino Acids", 1996.
A. Hadj Sassi, et al., Biochemical Engineering Journal, vol. 1, pp. 85-90, "FED-Batch Production of L-Lysine by *Corynebacterium Glutamicum*", 1998.
Bärbel Schrumpf, et al., Appl Microbiol Biotechnol, vol. 37, pp. 566-571, "Isolation and Prominent Characteristics of an L-Lysine Hyperproducing Strain of *Corynebacterium Glutamicum*", 1992.

* cited by examiner

*Primary Examiner*—James S Ketter
(74) *Attorney, Agent, or Firm*—Oblon, Spivak, McClelland, Maier & Neustadt, P.C.

(57) ABSTRACT

Isolated polynucleotide comprising a polynucleotide sequence chosen from the group consisting of a) polynucleotide which is identical to the extent of at least 70% to a polynucleotide which codes for a polypeptide which comprises the amino acid sequence of SEQ ID No. 2, b) polynucleotide which codes for a polypeptide which comprises an amino acid sequence which is identical to the extent of at least 70% to the amino acid sequence of SEQ ID No. 2, c) polynucleotide which is complementary to the polynucleotides of a) or b), and d) polynucleotide comprising at least 15 successive nucleotides of the polynucleotide sequence of a), b) or c), and a process for the fermentative preparation of L-amino acids using coryneform bacteria in which at least the lysR2 gene is present in attenuated form, and the use of the polynucleotide sequences as hybridization probes.

12 Claims, 1 Drawing Sheet

Figure 1: Plasmid map of pCR2.1lysR2int
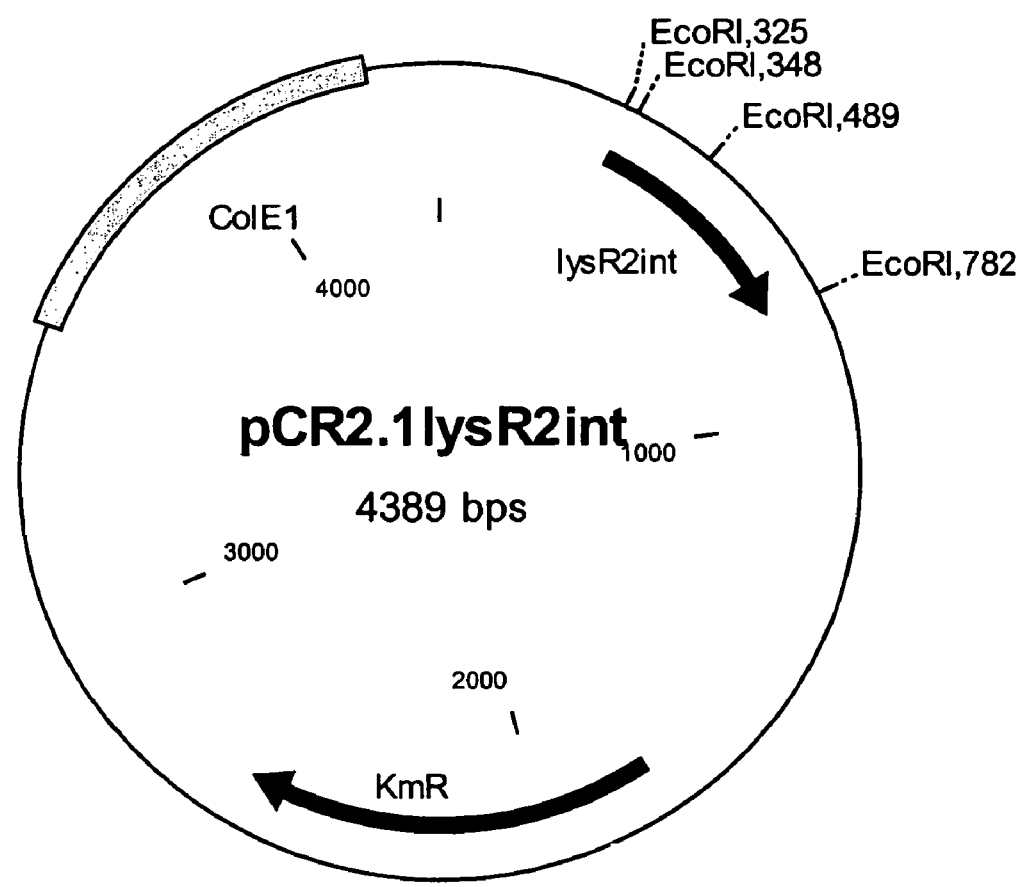

SEQUENCE LISTING

```
<160> NUMBER OF SEQ ID NOS: 5

<210> SEQ ID NO 1
<211> LENGTH: 1364
<212> TYPE: DNA
<213> ORGANISM: Corynebacterium glutamicum
<220> FEATURE:
<221> NAME/KEY: CDS
<222> LOCATION: (232)..(1161)
<223> OTHER INFORMATION:

<400> SEQUENCE: 1
cctgcgtgca ataaagacca ttgaaagcag caagaccggc ggccagcatc gcaaacacag      60
cgcgcttgta attgcgtgtt cctcgctcga tgccttcgtg gccttcgtgg ccttcgtgtg     120
cctcgacctt gctatctatt gcttggctca tggagttcat catgcgccaa cagcaaatat     180
tagtaaaatg ttagaaatag ctgttttga ttcactttgt gcatgtaggc t gtg acc        237
                                                        Val Thr
                                                          1
```

-continued

| | |
|---|---|
| atg ggc aac gac ggc gga gac ctg cga atc gac gac cta cgc agc ttc<br>Met Gly Asn Asp Gly Gly Asp Leu Arg Ile Asp Asp Leu Arg Ser Phe<br>       5                       10                    15 | 285 |
| att tca gtc gct caa tca ggc cac ctc acc gaa act gcc gaa aga tta<br>Ile Ser Val Ala Gln Ser Gly His Leu Thr Glu Thr Ala Glu Arg Leu<br>20                        25                    30 | 333 |
| ggc atc ccg cag ccc aca ctt tcc aga cga atc agc cga gtg gaa aaa<br>Gly Ile Pro Gln Pro Thr Leu Ser Arg Arg Ile Ser Arg Val Glu Lys<br>35                        40                  45                50 | 381 |
| cac gca ggc acc cca ctt ttc gac cgc gcc ggc cgc aaa ctc gtc ctc<br>His Ala Gly Thr Pro Leu Phe Asp Arg Ala Gly Arg Lys Leu Val Leu<br>                      55                  60                  65 | 429 |
| aac caa cga ggc cac gcc ttc ctc aac cac gcc agc gcc atc gtc gca<br>Asn Gln Arg Gly His Ala Phe Leu Asn His Ala Ser Ala Ile Val Ala<br>           70                       75                  80 | 477 |
| gaa ttc aac tcc gcc gca act gaa atc aaa cgc ctc atg gac cca gaa<br>Glu Phe Asn Ser Ala Ala Thr Glu Ile Lys Arg Leu Met Asp Pro Glu<br>85                        90                  95 | 525 |
| aaa ggc aca atc cga ctg gac ttc atg cat tcc ttg ggc act tgg atg<br>Lys Gly Thr Ile Arg Leu Asp Phe Met His Ser Leu Gly Thr Trp Met<br>100                       105                  110 | 573 |
| gtc ccc gaa ctt atc cga aca ttc cgc gcc gaa cac ccc aac gta gaa<br>Val Pro Glu Leu Ile Arg Thr Phe Arg Ala Glu His Pro Asn Val Glu<br>115                     120                  125              130 | 621 |
| ttc caa ctc cac caa gcg gca gca atg ctc ctg gta gat cgt gtt ttg<br>Phe Gln Leu His Gln Ala Ala Ala Met Leu Leu Val Asp Arg Val Leu<br>                       135                  140              145 | 669 |
| gct gat gaa act gac ctc gca tta gtt ggc ccc aaa cct gcc gag gtt<br>Ala Asp Glu Thr Asp Leu Ala Leu Val Gly Pro Lys Pro Ala Glu Val<br>                    150                  155              160 | 717 |
| ggt acc tct tta ggg tgg gcg cca ctg ctt cgt caa cga ctt gcc cta<br>Gly Thr Ser Leu Gly Trp Ala Pro Leu Leu Arg Gln Arg Leu Ala Leu<br>                   165                  170              175 | 765 |
| gct gtt ccc gca gat cac cgg ctt gcc tcc ttt tct ggc caa gga gaa<br>Ala Val Pro Ala Asp His Arg Leu Ala Ser Phe Ser Gly Gln Gly Glu<br>180                     185                  190 | 813 |
| ttg ccg ttg att act gcg gcg gaa gaa cct ttc gtg gcg atg cga gca<br>Leu Pro Leu Ile Thr Ala Ala Glu Glu Pro Phe Val Ala Met Arg Ala<br>195                     200                  205              210 | 861 |
| ggt ttc ggc acc cga ctc ctc atg gat gca tta gcc gaa gaa gcc ggt<br>Gly Phe Gly Thr Arg Leu Leu Met Asp Ala Leu Ala Glu Glu Ala Gly<br>                       215                  220              225 | 909 |
| ttt gtt ccc aat gtg gtt ttc gaa tcc atg gaa ctc acc acc gtc gca<br>Phe Val Pro Asn Val Val Phe Glu Ser Met Glu Leu Thr Thr Val Ala<br>                       230                  235              240 | 957 |
| ggg ctt gtc agc gca ggt ctc ggc gtt ggt gtg gtt ccg atg gat gat<br>Gly Leu Val Ser Ala Gly Leu Gly Val Gly Val Val Pro Met Asp Asp<br>                       245                  250              255 | 1005 |
| ccg tac ctt ccc aca gtg gga atc gtg caa cgc cca ctt agt cca ccc<br>Pro Tyr Leu Pro Thr Val Gly Ile Val Gln Arg Pro Leu Ser Pro Pro<br>260                     265                  270 | 1053 |
| gct tat agg gaa cta ggt ttg gtg tgg cga ctc aac gcg ggg ccg gca<br>Ala Tyr Arg Glu Leu Gly Leu Val Trp Arg Leu Asn Ala Gly Pro Ala<br>275                     280                  285              290 | 1101 |
| cct gcg gtg gat aac ttc cgg aag ttc gtg gcg gga tcg agg tat gca<br>Pro Ala Val Asp Asn Phe Arg Lys Phe Val Ala Gly Ser Arg Tyr Ala<br>                       295                  300              305 | 1149 |
| tta gaa gag ggc tgagctgtaa gtgtcgtggg tgccgtttta aggggttgag<br>Leu Glu Glu Gly<br>                310 | 1201 |

```
tttccccgat gactaggagt tggtccagat tgtgcgttag gggcccctag gggcgattct    1261
ggggctggtg tttttgtggc catgggggtt ggtgttaatc ctggaggctt gctgcaagat    1321
tgctgttaaa cttctcgtca cggatcgctt gggaagcctg gaa                      1364

<210> SEQ ID NO 2
<211> LENGTH: 310
<212> TYPE: PRT
<213> ORGANISM: Corynebacterium glutamicum

<400> SEQUENCE: 2

Val Thr Met Gly Asn Asp Gly Gly Asp Leu Arg Ile Asp Asp Leu Arg
1               5                   10                  15

Ser Phe Ile Ser Val Ala Gln Ser Gly His Leu Thr Glu Thr Ala Glu
            20                  25                  30

Arg Leu Gly Ile Pro Gln Pro Thr Leu Ser Arg Arg Ile Ser Arg Val
        35                  40                  45

Glu Lys His Ala Gly Thr Pro Leu Phe Asp Arg Ala Gly Arg Lys Leu
    50                  55                  60

Val Leu Asn Gln Arg Gly His Ala Phe Leu Asn His Ala Ser Ala Ile
65                  70                  75                  80

Val Ala Glu Phe Asn Ser Ala Ala Thr Glu Ile Lys Arg Leu Met Asp
                85                  90                  95

Pro Glu Lys Gly Thr Ile Arg Leu Asp Phe Met His Ser Leu Gly Thr
            100                 105                 110

Trp Met Val Pro Glu Leu Ile Arg Thr Phe Arg Ala Glu His Pro Asn
        115                 120                 125

Val Glu Phe Gln Leu His Gln Ala Ala Ala Met Leu Leu Val Asp Arg
    130                 135                 140

Val Leu Ala Asp Glu Thr Asp Leu Ala Leu Val Gly Pro Lys Pro Ala
145                 150                 155                 160

Glu Val Gly Thr Ser Leu Gly Trp Ala Pro Leu Leu Arg Gln Arg Leu
                165                 170                 175

Ala Leu Ala Val Pro Ala Asp His Arg Leu Ala Ser Phe Ser Gly Gln
            180                 185                 190

Gly Glu Leu Pro Leu Ile Thr Ala Ala Glu Glu Pro Phe Val Ala Met
        195                 200                 205

Arg Ala Gly Phe Gly Thr Arg Leu Leu Met Asp Ala Leu Ala Glu Glu
    210                 215                 220

Ala Gly Phe Val Pro Asn Val Val Phe Glu Ser Met Glu Leu Thr Thr
225                 230                 235                 240

Val Ala Gly Leu Val Ser Ala Gly Leu Gly Val Gly Val Val Pro Met
                245                 250                 255

Asp Asp Pro Tyr Leu Pro Thr Val Gly Ile Val Gln Arg Pro Leu Ser
            260                 265                 270

Pro Pro Ala Tyr Arg Glu Leu Gly Leu Val Trp Arg Leu Asn Ala Gly
        275                 280                 285

Pro Ala Pro Val Asp Asn Phe Arg Lys Phe Val Ala Gly Ser Arg
    290                 295                 300

Tyr Ala Leu Glu Glu Gly
305                 310

<210> SEQ ID NO 3
<211> LENGTH: 439
<212> TYPE: DNA
```

-continued

```
<213> ORGANISM: Corynebacterium glutamicum

<400> SEQUENCE: 3
ccatcgtcgc agaattcaac tccgccgcaa ctgaaatcaa acgcctcatg gacccagaaa      60
aaggcacaat ccgactggac ttcatgcatt ccttgggcac ttggatggtc cccgaactta    120
tccgaacatt ccgcgccgaa caccccaacg tagaattcca actccaccaa gcggcagcaa    180
tgctcctggt agatcgtgtt ttggctgatg aaactgacct cgcattagtt ggccccaaac    240
ctgccgaggt tggtacctct ttagggtggg cgccactgct tcgtcaacga cttgccctag    300
ctgttcccgc agatcaccgg cttgcctcct tttctggcca aggagaattg ccgttgatta    360
ctgcggcgga agaacctttc gtggcgatgc gagcaggttt cggcacccga ctcctcatgg    420
atgcattagc cgaagaagc                                                 439

<210> SEQ ID NO 4
<211> LENGTH: 20
<212> TYPE: DNA
<213> ORGANISM: Corynebacterium glutamicum

<400> SEQUENCE: 4
ccatcgtcgc agaattcaac                                                 20

<210> SEQ ID NO 5
<211> LENGTH: 20
<212> TYPE: DNA
<213> ORGANISM: Corynebacterium glutamicum

<400> SEQUENCE: 5
gcttcttcgg ctaatgcatc                                                 20
```

NUCLEOTIDE SEQUENCES FOR ENCODING OF THE LYSR2-GENE

The invention provides nucleotide sequences from coryneform bacteria which code for the lysR2 gene and a process for the fermentative preparation of amino acids, in particular L-lysine and L-valine, by attenuation of the lysR2 gene. The lysR2 gene codes for the LysR2 protein, which is a transcription regulator of the LysR family.

PRIOR ART

L-Amino acids, in particular L-lysine and L-valine, are used in human medicine and in the pharmaceuticals industry, in the foodstuffs industry and very particularly in animal nutrition.

It is known that amino acids are prepared by fermentation from strains of coryneform bacteria, in particular *Corynebacterium glutamicum*. Because of their great importance, work is constantly being undertaken to improve the preparation processes. Improvements to the process can relate to fermentation measures, such as, for example, stirring and supply of oxygen, or the composition of the nutrient media, such as, for example, the sugar concentration during the fermentation, or the working up to the product form by, for example, ion exchange chromatography, or the intrinsic output properties of the microorganism itself.

Methods of mutagenesis, selection and mutant selection are used to improve the output properties of these microorganisms. Strains which are resistant to antimetabolites or are auxotrophic for metabolites of regulatory importance and which produce amino acids are obtained in this manner.

Methods of the recombinant DNA technique have also been employed for some years for improving the strain of *Corynebacterium* strains which produce L-amino acids.

OBJECT OF THE INVENTION

The inventors had the object of providing new measures for improved fermentative preparation of amino acids, in particular L-lysine and L-valine.

DESCRIPTION OF THE INVENTION

The invention provides an isolated polynucleotide from coryneform bacteria, comprising a polynucleotide sequence which codes for the lysR2 gene, chosen from the group consisting of a) polynucleotide which is identical to the extent of at least 70% to a polynucleotide which codes for a polypeptide which comprises the amino acid sequence of SEQ ID No. 2, b) polynucleotide which codes for a polypeptide which comprises an amino acid sequence which is identical to the extent of at least 70% to the amino acid sequence of SEQ ID No. 2, c) polynucleotide which is complementary to the polynucleotides of a) or b), and d) polynucleotide comprising at least 15 successive nucleotides of the polynucleotide sequence of a), b) or c), the polypeptide preferably having the activity of the transcription regulator LysR2.

The invention also provides the abovementioned polynucleotide, this preferably being a DNA which is capable of replication, comprising:

(i) the nucleotide sequence shown in SEQ ID No. 1 or (ii) at least one sequence which corresponds to sequence (i) within the range of the degeneration of the genetic code, or (iii) at least one sequence which hybridizes with the sequences complementary to sequences (i) or (ii), and optionally (iv) sense mutations of neutral function in (i) which do not modify the activity of the protein/polypeptide.

The invention also provides a) polynucleotides comprising at least 15 successive nucleotides chosen from the nucleotide sequence of SEQ ID No. 1 between positions 1 and 231, b) polynucleotides comprising at least 15 successive nucleotides chosen from the nucleotide sequence of SEQ ID No. 1 between positions 232 and 1161, c) polynucleotides comprising at least 15 successive nucleotides chosen from the nucleotide sequence of SEQ ID No. 1 between positions 1162 and 1364.

The invention also provides:

a polynucleotide, in particular DNA, which is capable of replication and comprises the nucleotide sequence as shown in SEQ ID No. 1;

a polynucleotide which codes for a polypeptide which comprises the amino acid sequence as shown in SEQ ID No. 2;

a vector containing parts of the polynucleotide according to the invention, but at least 15 successive nucleotides of the sequence claimed and coryneform bacteria in which the lysR2 gene is attenuated, in particular by an insertion or deletion.

The invention also provides polynucleotides which substantially comprise a polynucleotide sequence, which are obtainable by screening by means of hybridization of a corresponding gene library, which comprises the complete gene with the polynucleotide sequence corresponding to SEQ ID No. 1, with a probe which comprises the sequence of the polynucleotide mentioned, according to SEQ ID No. 1 or a fragment thereof, and isolation of the DNA sequence mentioned.

Polynucleotide sequences according to the invention are suitable as hybridization probes for RNA, cDNA and DNA, in order to isolate, in the full length, nucleic acids, or polynucleotides or genes which code for the LysR2 protein or to isolate those nucleic acids or polynucleotides or genes which have a high similarity with the sequence of the lysR2 gene. They are also suitable for incorporation into so-called "arrays", "micro arrays" or DNA chips in order to detect and determine the corresponding polynucleotides.

Polynucleotide sequences according to the invention are furthermore suitable as primers with the aid of which DNA of genes which code for the LysR2 protein can be prepared with the polymerase chain reaction (PCR).

Such oligonucleotides which serve as probes or primers comprise at least 25, 26, 27, 28, 29 or 30, preferably at least 20, 21, 22, 23 or 24, very particularly preferably at least 15, 16, 17, 18 or 19 successive nucleotides. Oligonucleotides with a length of at least 31, 32, 33, 34, 35, 36, 37, 38, 39 or 40, or at least 41, 42, 43, 44, 45, 46, 47, 48, 49 or 50 nucleotides are also suitable. Oligonucleotides with a length of at least 100, 150, 200, 250 or 300 nucleotides are optionally also suitable.

"Isolated" means separated out of its natural environment.

"Polynucleotide" in general relates to polyribonucleotides and polydeoxyribonucleotides, it being possible for these to be non-modified RNA or DNA or modified RNA or DNA.

The polynucleotides according to the invention include a polynucleotide according to SEQ ID No. 1 or a fragment prepared therefrom and also those which are at least 70% to 80%, preferably at least 81% to 85%, particularly preferably at least 86% to 90% and very particularly preferably at least 91%, 93%, 95%, 97% or 99% identical to the polynucleotide according to SEQ ID No. 1 or a fragment prepared therefrom.

"Polypeptides" are understood as meaning peptides or proteins which comprise two or more amino acids bonded via peptide bonds.

The polypeptides according to the invention include a polypeptide according to SEQ ID No. 2, in particular those with the biological activity of the LysR2 protein, and also those which are at least 70% to 80%, preferably at least 81% to 85% and in particular at least 86% to 90% and very particularly preferably at least 91%, 93%, 95%, 97% or 99% identical to the polypeptide according to SEQ. ID No. 2 and have the activity mentioned.

The invention furthermore relates to a process for the fermentative preparation of amino acids chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine, in particular L-lysine and L-valine, using coryneform bacteria which in particular already produce amino acids and in which the nucleotide sequences which code for the lysR2 gene are attenuated, in particular eliminated or expressed at a low level.

The term "attenuation" in this connection describes the reduction or elimination of the intracellular activity of one or more enzymes (proteins) in a microorganism which are coded by the corresponding DNA, for example by using a weak promoter or using a gene or allele which codes for a corresponding enzyme with a low activity or inactivates the corresponding gene or allele or enzyme (protein), and optionally combining these measures.

The microorganisms which the present invention provides can prepare amino acids, in particular L-lysine and L-valine, from glucose, sucrose, lactose, fructose, maltose, molasses, starch, cellulose or from glycerol and ethanol. They can be representatives of coryneform bacteria, in particular of the genus *Corynebacterium*. Of the genus *Corynebacterium*, there may be mentioned in particular the species *Corynebacterium glutamicum*, which is known among experts for its ability to produce L-amino acids.

Suitable strains of the genus *Corynebacterium*, in particular of the species *Corynebacterium glutamicum* (*C. glutamicum*), are in particular the known wild-type strains
    *Corynebacterium glutamicum* ATCC13032
    *Corynebacterium acetoglutamicum* ATCC15806
    *Corynebacterium acetoacidophilum* ATCC13870
    *Corynebacterium melassecola* ATCC17965
    *Corynebacterium thermoaminogenes* FERM BP-1539
    *Brevibacterium flavum* ATCC14067
    *Brevibacterium lactofermentum* ATCC13869 and
    *Brevibacterium divaricatum* ATCC14020 or L-amino acid-producing mutants or strains prepared therefrom, such as, for example, the L-lysine-producing strains
    *Corynebacterium glutamicum* FERM-P 1709
    *Brevibacterium flavum* FERM-P 1708
    *Brevibacterium lactofermentum* FERM-P 1712
    *Corynebacterium glutamicum* FERM-P 6463
    *Corynebacterium glutamicum* FERM-P 6464
    *Corynebacterium glutamicum* DM58-1
    *Corynebacterium glutamicum* DG52-5
    *Corynebacterium glutamicum* DSM 5715 and
    *Corynebacterium glutamicum* DSM 12866 or such as, for example, the L-valine-producing strains
    *Corynebacterium glutamicum* DSM 12455
    *Corynebacterium glutamicum* FERM-P 9325
    *Brevibacterium lactofermentum* FERM-P 9324
    *Brevibacterium lactofermentum* FERM-BP 1763.

The inventors have succeeded in isolating the new lysR2 gene of *C. glutamicum* which codes for the LysR2 protein, which is a transcription regulator of the LysR family.

To isolate the lysR2 gene or also other genes of *C. glutamicum*, a gene library of this microorganism is first set up in *Escherichia coli* (*E. coli*). The setting up of gene libraries is described in generally known textbooks and handbooks. The textbook by Winnacker: Gene und Klone, Eine Einführung in die Gentechnologie [Genes and Clones, An Introduction to Genetic Engineering] (Verlag Chemie, Weinheim, Germany, 1990), or the handbook by Sambrook et al.: Molecular Cloning, A Laboratory Manual (Cold Spring Harbor Laboratory Press, 1989) may be mentioned as an example. A well-known gene library is that of the *E. coli* K-12 strain W3110 set up in λ vectors by Kohara et al. (Cell 50, 495-508 (1987)). Bathe et al. (Molecular and General Genetics, 252:255-265, 1996) describe a gene library of *C. glutamicum* ATCC13032, which was set up with the aid of the cosmid vector SuperCos I (Wahl et al., 1987, Proceedings of the National Academy of Sciences USA, 84:2160-2164) in the *E. coli* K-12 strain NM554 (Raleigh et al., 1988, Nucleic Acids Research 16:1563-1575). Börmann et al. (Molecular Microbiology 6(3), 317-326)) (1992)) in turn describe a gene library of *C. glutamicum* ATCC13032 using the cosmid pHC79 (Hohn and Collins, 1980, Gene 11, 291-298).

To prepare a gene library of *C. glutamicum* in *E. coli* it is also possible to use plasmids such as pBR322 (Bolivar, 1979, Life Sciences, 25, 807-818) or pUC9 (Vieira et al., 1982, Gene, 19:259-268). Suitable hosts are, in particular, those *E. coli* strains which are restriction- and recombination-defective, such as, for example, the strain DH5α (Jeffrey H. Miller: "A Short Course in Bacterial Genetics, A Laboratory Manual and Handbook for *Escherichia coli* and Related Bacteria", Cold Spring Harbour [sic] Laboratory Press, 1992).

The long DNA fragments cloned with the aid of cosmids or other λ vectors can then be subcloned in turn into the usual vectors suitable for DNA sequencing.

Methods of DNA sequencing are described, inter alia, by Sanger et al. (Proceedings of the National Academy of Sciences of the United States of America USA, 74:5463-5467, 1977).

The resulting DNA sequences can then be investigated with known algorithms or sequence analysis programs, such as e.g. that of Staden (Nucleic Acids Research 14, 217-232 (1986)), that of Marck (Nucleic Acids Research 16, 1829-1836 (1988)) or the GCG program of Butler (Methods of Biochemical Analysis 39, 74-97 (1998)).

The new DNA sequence of *C. glutamicum* which codes for the lysR2 gene and which, as SEQ ID No. 1, is a constituent of the present invention has been obtained in this manner. The amino acid sequence of the corresponding protein has furthermore been derived from the present DNA sequence by the methods described above. The resulting amino acid sequence of the lysR2 gene product is shown in SEQ ID No. 2. It is known that enzymes endogenous in the host can split off the N-terminal amino acid methionine or formylmethionine of the protein formed.

Coding DNA sequences which result from SEQ ID No. 1 by the degeneracy of the genetic code are also a constituent of the invention. In the same way, DNA sequences which hybridize with SEQ ID No. 1 or parts of SEQ ID No. 1 are a constituent of the invention. Conservative amino acid exchanges, such as e.g. exchange of glycine for alanine or of aspartic acid for glutamic acid in proteins, are furthermore known among experts as "sense mutations" which do not lead to a fundamental change in the activity of the protein, i.e. are of neutral function. It is furthermore known that changes on the N and/or C terminus of a protein cannot substantially impair or can even stabilize the function thereof. Information in this context can be found by the expert, inter alia, in Ben-Bassat et al. (Journal of Bacteriology 169:751-757 (1987)), in O'Regan et al. (Gene 77:237-251 (1989)), in Sahin-Toth et al. (Protein Sciences 3:240-247 (1994)), in Hochuli et al. (Bio/Technology 6:1321-1325 (1988)) and in known textbooks of genetics and molecular biology. Amino acid sequences which result in a corresponding manner from SEQ ID No. 2 are also a constituent of the invention.

Finally, DNA sequences which are prepared by the polymerase chain reaction (PCR) using primers which result from SEQ ID No. 1 are a constituent of the invention. Such oligonucleotides typically have a length of at least 15 nucleotides.

Instructions for identifying DNA sequences by means of hybridization can be found by the expert, inter alia, in the handbook "The DIG System Users Guide for Filter Hybridization" from Boehringer Mannheim GmbH (Mannheim, Germany, 1993) and in Liebl et al. (International Journal of Systematic Bacteriology 41: 255-260 (1991)). Instructions for amplification of DNA sequences with the aid of the polymerase chain reaction (PCR) can be found by the expert, inter alia, in the handbook by Gait: Oligonukleotide [sic] synthesis: A Practical Approach (IRL Press, Oxford, UK, 1984) and in Newton and Graham: PCR (Spektrum Akademischer Verlag, Heidelberg, Germany, 1994).

In the work on the present invention, it has been found that coryneform bacteria produce amino acids, in particular L-lysine and L-valine, in an improved manner after attenuation of the lysR2 gene.

To achieve an attenuation, either the expression of the lysR2 gene or the catalytic properties of the enzyme protein can be reduced or eliminated. The two measures can optionally be combined.

The reduction in gene expression can take place by suitable culturing or by genetic modification (mutation) of the signal structures of gene expression. Signal structures of gene expression are, for example, repressor genes, activator genes, operators, promoters, attenuators, ribosome binding sites, the start codon and terminators. The expert can find information on this e.g. in the patent application WO 96/15246, in Boyd and Murphy (Journal of Bacteriology 170: 5949 (1988)), in Voskuil and Chambliss (Nucleic Acids Research 26: 3548 (1998), in Jensen and Hammer (Biotechnology and Bioengineering 58: 191 (1998)), in Pátek et al. (Microbiology 142: 1297 (1996)), Vasicova et al. (Journal of Bacteriology 181: 6188 (1999)) and in known textbooks of genetics and molecular biology, such as e.g. the textbook by Knippers ("Molekulare Genetik [Molecular Genetics]", 6th edition, Georg Thieme Verlag, Stuttgart, Germany, 1995) or that by Winnacker ("Gene und Klone [Genes and Clones]", VCH Verlagsgesellschaft, Weinheim, Germany, 1990).

Mutations which lead to a change or reduction in the catalytic properties of enzyme proteins are known from the prior art; examples which may be mentioned are the works by Qiu and Goodman (Journal of Biological Chemistry 272: 8611-8617 (1997)), Sugimoto et al. (Bioscience Biotechnology and Biochemistry 61: 1760-1762 (1997)) and Möckel ("Die Threonindehydratase aus *Corynebacterium glutamicum*: Aufhebung der allosterischen Regulation und Struktur des Enzyms [Threonine dehydratase from *Corynebacterium glutamicum*: Cancelling the allosteric regulation and structure of the enzyme]", Reports from the Jülich Research Centre, Jül-2906, ISSN09442952, Jülich, Germany, 1994). Summarizing descriptions can be found in known textbooks of genetics and molecular biology, such as e.g. that by Hagemann ("Aligemeine Genetik [General Genetics]", Gustav Fischer Verlag, Stuttgart, 1986).

Possible mutations are transitions, transversions, insertions and deletions. Depending on the effect of the amino acid exchange on the enzyme activity, missense mutations or nonsense mutations are referred to. Insertions or deletions of at least one base pair (bp) in a gene lead to frame shift mutations, as a consequence of which incorrect amino acids are incorporated or translation is interrupted prematurely. Deletions of several codons typically lead to a complete loss of the enzyme activity. Instructions on generation of such mutations are prior art and can be found in known textbooks of genetics and molecular biology, such as e.g. the textbook by Knippers ("Molekulare Genetik [Molecular Genetics]", 6th edition, Georg Thieme Verlag, Stuttgart, Germany, 1995), that by Winnacker ("Gene und Klone [Genes and Clones]", VCH Verlagsgesellschaft, Weinheim, Germany, 1990) or that by Hagemann ("Allgemeine Genetik [General Genetics]", Gustav Fischer Verlag, Stuttgart, 1986).

A common method of mutating genes of *C. glutamicum* is the method of gene disruption and gene replacement described by Schwarzer and Pühler (Bio/Technology 9, 84-87 (1991)).

In the method of gene disruption a central part of the coding region of the gene of interest is cloned in a plasmid vector which can replicate in a host (typically *E. coli*), but not in *C. glutamicum*. Possible vectors are, for example, pSUP301 (Simon et al., Bio/Technology 1, 784-791 (1983)), pK18mob or pK19mob (Schäfer et al., Gene 145, 69-73 (1994)), pK18mobsacB or pK19mobsacB (Jäger et al., Journal of Bacteriology 174: 5462-65 (1992)), pGEM-T (Promega corporation, Madison, Wis., USA), pCR2.1-TOPO (Shuman (1994). Journal of Biological Chemistry 269:32678-84; U.S. Pat. No. 5,487,993), pCR®Blunt (Invitrogen, Groningen, The Netherlands; Bernard et al., Journal of Molecular Biology, 234: 534-541 (1993)) or pEM1 (Schrumpf et al, 1991, Journal of Bacteriology 173:4510-4516). The plasmid vector which contains the central part of the coding region of the gene is then transferred into the desired strain of *C. glutamicum* by conjugation or transformation. The method of conjugation is described, for example, by Schäfer et al. (Applied and Environmental Microbiology 60, 756-759 (1994)). Methods for transformation are described, for example, by Thierbach et al. (Applied Microbiology and Biotechnology 29, 356-362 (1988)), Dunican and Shivnan (Bio/Technology 7, 1067-1070 (1989)) and Tauch et al. (FEMS Microbiological Letters 123, 343-347 (1994)). After homologous recombination by means of a "cross-over" event, the coding region of the gene in question is interrupted by the vector sequence and two incomplete alleles are obtained, one lacking the 3' end and one lacking the 5' end. This method has been used, for example, by Fitzpatrick et al. (Applied Microbiology and Biotechnology 42, 575-580 (1994)) to eliminate the recA gene of *C. glutamicum*.

FIG. 1 shows by way of example the plasmid vector pCR2.1lysR2int, with the aid of which the lysR2 gene can be disrupted or eliminated.

In the method of gene replacement, a mutation, such as e.g. a deletion, insertion or base exchange, is established in vitro in the gene of interest. The allele prepared is in turn cloned in a vector which is not replicative for *C. glutamicum* and this is then transferred into the desired host of *C. glutamicum* by transformation or conjugation. After homologous recombination by means of a first "cross-over" event which effects integration and a suitable second "cross-over" event which effects excision in the target gene or in the target sequence, the incorporation of the mutation or of the allele is achieved. This method was used, for example, by Peters-Wendisch et al. (Microbiology 144, 915-927 (1998)) to eliminate the pyc gene of *C. glutamicum* by a deletion.

A deletion, insertion or a base exchange can be incorporated into the lysR2 gene in this manner.

In addition, it may be advantageous for the production of L-amino acids, in particular L-lysine and L-valine, to enhance, in particular to over-express, one or more enzymes of the particular biosynthesis pathway, of glycolysis, of anaplerosis, of the pentose phosphate cycle or of amino acid export, in addition to attenuation of the lysR2 gene.

The term "enhancement" in this connection describes the increase in the intracellular activity of one or more enzymes (proteins) in a microorganism which are coded by the corresponding DNA, for example by increasing the number of copies of the gene or genes, using a potent promoter or using a gene or allele which codes for a corresponding enzyme (protein) having a high activity, and optionally combining these measures.

Thus, for example, for the preparation of L-lysine, at the same time one or more of the genes chosen from the group consisting of the dapA gene which codes for dihydrodipicolinate synthase (EP-B 0 197 335), the eno gene which codes for enolase (DE: 19947791.4), the zwf gene which codes for the zwf gene product (JP-A-09224661), the pyc gene which codes for pyruvate carboxylase (Peters-Wendisch et al. (Microbiology 144, 915-927 (1998))

the lysE gene which codes for lysine export (DE-A-195 48 222)

the lysC gene which codes for a feed back resistant aspartate kinase (EP-B-0387527; EP-A-069975.9)

the zwa1 gene which codes for the Zwa1 protein (DE: 199 59 328.0, DSM 13115)

can be enhanced, in particular over-expressed.

Thus, for example, for the production of L-valine, at the same time one or more of the genes or alleles chosen from the group consisting of at the same time the ilvBN gene which codes for acetohydroxy-acid synthase (Keilhauer et al., (1993) Journal of Bacteriology 175: 5595-5603), or at the same time the ilvD gene which codes for dihydroxy-acid dehydratase (Sahm and Eggeling (1999) Applied and Environmental Microbiology 65: 1973-1979), or at the same time the mqo gene which codes for malate: quinone oxidoreductase (Molenaar et al., European Journal of Biochemistry 254, 395-403 (1998))

can be enhanced, in particular over-expressed.

It may furthermore be advantageous for the production of amino acids, in particular L-lysine, in addition to the attenuation of the lysR2 gene, at the same time for one or more of the genes chosen from the group consisting of the pck gene which codes for phosphoenol pyruvate carboxykinase (DE 199 50 409.1, DSM 13047), the pgi gene which codes for glucose 6-phosphate isomerase (U.S. Ser. No. 09/396,478, DSM 12969), the poxB gene which codes for pyruvate oxidase (DE:1995 1975.7, DSM 13114)

the zwa2 gene which codes for the Zwa2 protein (DE: 19959327.2, DSM 13113), to be attenuated, in particular eliminated.

Finally, it may be advantageous for the production of L-lysine, in addition to the attenuation of the lysR2 gene, at the same time for one or more of the genes chosen from the group consisting of the hom gene which codes for homoserine dehydrogenase (EP-A-0131171), the thrB gene which codes for homoserine kinase (Peoples, O. W., et al., Molecular Microbiology 2 (1988): 63-72), and the panD gene which codes for aspartate decarboxylase (EP-A-1006192)

to be attenuated, in particular eliminated.

The attenuation of homoserine dehydrogenase can also be achieved, inter alia, by amino acid exchanges, such as, for example, by exchange of L-valine for L-alanine, L-glycine or L-leucine in position 59 of the enzyme protein, by exchange of L-valine by L-isoleucine, L-valine or L-leucine in position 104 of the enzyme protein and/or by exchange of L-asparagine by L-threonine or L-serine in position 118 of the enzyme protein.

The attenuation of homoserine kinase can also be achieved, inter alia, by amino acid exchanges, such as, for example, by exchange of L-alanine for L-valine, L-glycine or L-leucine in position 133 of the enzyme protein and/or by exchange of L-proline by L-threonine, L-isoleucine or L-serine in position 138 of the enzyme protein.

The attenuation of aspartate decarboxylase can also be achieved, inter alia, by amino acid exchanges, such as, for example, by exchanges of L-alanine for L-glycine, L-valine or L-isoleucine in position 36 of the enzyme protein.

In addition to attenuation of the lysR2 gene it may furthermore be advantageous, for the production of amino acids, in particular L-lysine and L-valine, to eliminate undesirable side reactions, (Nakayama: "Breeding of Amino Acid Producing Micro-organisms", in: Overproduction of Microbial Products, Krumphanzl, Sikyta, Vanek (eds.), Academic Press, London, UK, 1982).

The invention also provides the microorganisms prepared according to the invention, and these can be cultured continuously or discontinuously in the batch process (batch culture) or in the fed batch (feed process) or repeated fed batch process (repetitive feed process) for the purpose of production of L-amino acids, in particular L-lysine and L-valine. A summary of known culture methods are [sic] described in the textbook by Chmiel (Bioprozesstechnik 1. Einführung in die Bioverfahrenstechnik [Bioprocess Technology 1. Introduction to Bioprocess Technology (Gustav Fischer Verlag, Stuttgart, 1991)) or in the textbook by Storhas (Bioreaktoren und periphere Einrichtungen [Bioreactors and Peripheral Equipment] (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981). Sugars and carbohydrates, such as e.g. glucose, sucrose, lactose, fructose, maltose, molasses, starch and cellulose, oils and fats, such as, for example, soya oil, sunflower oil, groundnut oil and coconut fat, fatty acids, such as, for example, palmitic acid, stearic acid and linoleic acid, alcohols, such as, for example, glycerol and ethanol, and organic acids, such as, for example, acetic acid, can be used as the source of carbon. These substances can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus. The culture medium must furthermore comprise salts of metals, such as, for example, magnesium sulfate or iron sulfate, which are necessary for growth. Finally, essential growth substances, such as amino acids and vitamins, can be employed in addition to the abovementioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH of the culture. Antifoams, such as, for example, fatty acid polyglycol esters, can be employed to control the development of foam. Suitable substances having a selective action, such as, for example, antibiotics, can be added to the medium to maintain the stability of plasmids. To maintain aerobic conditions, oxygen or oxygen-containing gas mixtures, such as, for example, air, are introduced into the culture. The temperature of the culture is usually 20° C. to 45° C., and preferably 25° C. to 40° C. Culturing is continued until a maximum of the desired product has formed. This target is usually reached within 10 hours to 160 hours.

Methods for the determination of L-amino acids are known from the prior art. The analysis can thus be carried out, for example, as described by Spackman et al. (Analytical Chemistry, 30, (1958) 1190) by anion exchange chromatography with subsequent ninhydrin derivatization, or it can be carried out by reversed phase HPLC, for example as described by Lindroth et al. (Analytical Chemistry (1979) 51: 1167-1174).

A pure culture of the following microorganism was deposited on 28th Jul. 2000 at the Deutsche Sammlung für Mikroorganismen und Zellkulturen (DSMZ=German Collection of Microorganisms and Cell Cultures, Braunschweig, Germany) in accordance with the Budapest Treaty:

*Escherichia coli* strain TOP10F/pCR2.11ysR2int as DSM 13617.

The process according to the invention is used for the fermentative preparation of amino acids, in particular L-lysine and L-valine.

The present invention is explained in more detail in the following with the aid of embodiment examples.

The isolation of plasmid DNA from *Escherichia coli* and all techniques of restriction, Klenow and alkaline phosphatase treatment were carried out by the method of Sambrook et al. (Molecular Cloning. A Laboratory Manual (1989) Cold Spring Harbour [sic] Laboratory Press, Cold Spring Harbor, N.Y., USA). Methods for transformation of *Escherichia coli* are also described in this handbook.

The composition of the usual nutrient media, such as LB or TY medium, can also be found in the handbook by Sambrook et al.

EXAMPLE 1

Preparation of a Genomic Cosmid Gene Library From *C. glutamicum* ATCC 13032

Chromosomal DNA from *C. glutamicum* ATCC 13032 was isolated as described by Tauch et al. (1995, Plasmid 33:168-179) and partly cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Molecular Biochemicals, Mannheim, Germany, Product Description SAP, Code no. 1758250). The DNA of the cosmid vector SuperCos1 (Wahl et al., 1987, Proceedings of the National Academy of Sciences, USA 84:2160-2164), obtained from Stratagene (La Jolla, USA, Product Description SuperCos1 Cosmid Vector Kit, Code no. 251301) was cleaved with the restriction enzyme XbaI (Amersham Pharmacia, Freiburg, Germany, Product Description XbaI, Code no. 27-0948-02) and likewise dephosphorylated with shrimp alkaline phosphatase.

The cosmid DNA was then cleaved with the restriction enzyme BamHI (Amersham Pharmacia, Freiburg, Germany, Product Description BamHI, Code no. 27-0868-04). The cosmid DNA treated in this manner was mixed with the treated ATCC13032 DNA and the batch was treated with T4 DNA ligase (Amersham Pharmacia, Freiburg, Germany, Product Description T4-DNA-Ligase, Code no. 27-0870-04). The ligation mixture was then packed in phages with the aid of Gigapack II XL Packing Extract (Stratagene, La Jolla, USA, Product Description Gigapack II XL Packing Extract, Code no. 200217).

For infection of the *E. coli* strain. NM554 (Raleigh et al. 1988, Nucleic Acid Res. 16:1563-1575) the cells were taken up in 10 MM $MgSO_4$ and mixed with an aliquot of the phage suspension. The infection and titering of the cosmid library were carried out as described by Sambrook et al. (1989, Molecular Cloning: A laboratory Manual, Cold Spring Harbor), the cells being plated out on LB agar (Lennox, 1955, Virology, 1:190) +100 µg/ml ampicillin. After incubation overnight at 37° C., recombinant individual clones were selected.

EXAMPLE 2

Isolation and Sequencing of the lysR2 Gene

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Molecular Biochemicals, Mannheim, Germany, Product Description SAP, Product No. 1758250). After separation by gel electrophoresis, the cosmid fragments in the size range of 1500 to 2000 bp were isolated with the QiaExII Gel Extraction Kit (Product No. 20021, Qiagen, Hilden, Germany).

The DNA of the sequencing vector pZero-1, obtained from Invitrogen (Groningen, The Netherlands, Product Description Zero Background Cloning Kit, Product No. K2500-01) was cleaved with the restriction enzyme BamHI (Amersham Pharmacia, Freiburg, Germany, Product Description BamHI, Product No. 27-0868-04). The ligation of the cosmid fragments in the sequencing vector pZero-1 was carried out as described by Sambrook et al. (1989, Molecular Cloning: A Laboratory Manual, Cold Spring Harbor), the DNA mixture being incubated overnight with T4 ligase (Pharmacia Biotech, Freiburg, Germany). This ligation mixture was then electroporated (Tauch et al. 1994, FEMS Microbiol Letters, 123:343-7) into the *E. coli* strain DH5αMCR (Grant, 1990, Proceedings of the National Academy of Sciences, U.S.A., 87:4645-4649) and plated out on LB agar (Lennox, 1955, Virology, 1:190) with 50 µg/ml zeocin.

The plasmid preparation of the recombinant clones was carried out with Biorobot 9600 (Product No. 900200, Qiagen, Hilden, Germany). The sequencing was carried out by the dideoxy chain termination method of Sanger et al. (1977, Proceedings of the National Academies of Sciences, U.S.A., 74:5463-5467) with modifications according to Zimmermann et al. (1990, Nucleic Acids Research, 18:1067). The "RR dRhodamin Terminator Cycle Sequencing Kit" from PE Applied Biosystems (Product No. 403044, Weiterstadt, Germany) was used. The separation by gel electrophoresis and analysis of the sequencing reaction were carried out in a "Rotiphoresis NF Acrylamide/Bisacrylamide" Gel (29:1) (Product No. A124.1, Roth, Karlsruhe, Germany) with the "ABI Prism 377" sequencer from PE Applied Biosystems (Weiterstadt, Germany).

The raw sequence data obtained were then processed using the Staden program package (1986, Nucleic Acids Research, 14:217-231) version 97-0. The individual sequences of the pZeroI derivatives were assembled to a continuous contig. The computer-assisted coding region analysis [sic] were prepared with the XNIP program (Staden, 1986, Nucleic Acids Research, 14:217-231). Further analyses were carried out with the "BLAST search program" (Altschul et al., 1997, Nucleic Acids Research, 25:3389-3402) against the non-redundant databank of the "National Center for Biotechnology Information" (NCBI, Bethesda, Md., USA).

The resulting nucleotide sequence is shown in SEQ ID No. 1. Analysis of the nucleotide sequence showed an open reading frame of 933 base pairs, which was called the lysR2 gene. The lysR2 gene codes for a polypeptide of 310 amino acids.

EXAMPLE 3

Preparation of an Integration Vector for Integration Mutagenesis of the lysR2 Gene From the strain ATCC 13032, chromosomal DNA was isolated by the method of Eikmanns et al. (Microbiology 140: 1817-1828 (1994)). On the basis of the sequence of the lysR2 gene known for *C. glutamicum* from example 2, the following oligonucleotides were chosen for the polymerase chain reaction (see SEQ ID No. 4 and SEQ ID No. 5):

```
lysR2intA:
5' CCA TCG TCG GAG AAT TCA AC 3' lysR2intB:
5' GCT TCT TCG GCT AAT GCA TC 3'
```

The primers shown were synthesized by MWG Biotech (Ebersberg, Germany) and the PCR reaction was carried out by the standard PCR method of Innis et al. (PCR protocols. A guide to methods and applications, 1990, Academic Press) with Pwo-Polymerase from Boehringer. With the aid of the polymerase chain reaction, an internal fragment of the lysR2 gene 439 bp in size was isolated, this being shown in SEQ ID No. 3.

The amplified DNA fragment was ligated with the TOPO TA Cloning Kit from Invitrogen Corporation (Carlsbad, Calif., USA; Catalogue Number K4500-01) in the vector pCR2.1-TOPO (Mead at al. (1991) Bio/Technology 9:657-663).

The *E. coli* strain TOP10F was then transformed with the ligation batch (Hanahan, In: DNA cloning. A practical approach. Vol. I, IRL-Press, Oxford, Washington DC, USA, 1985). Selection of plasmid-carrying cells was made by plating out the transformation batch on LB agar (Sambrook et al., Molecular cloning: A Laboratory Manual. $2^{nd}$ Ed. Cold Spring Harbor Laboratory Press, Cold Spring Harbor, N.Y., 1989), which had been supplemented with 25 mg/l kanamycin. Plasmid DNA was isolated from a transformant with the aid of the QIAprep Spin Miniprep Kit from Qiagen and checked by restriction with the restriction enzyme EcoRI and subsequent agarose gel electrophoresis (0.8%). The plasmid was called pCR2.1lysR2int.

EXAMPLE 4

Integration Mutagenesis of the lysR2 Gene in the Lysine Producer DSM 5715 and in the Valine Producer FERM BP-1763

The vector pCR2.1lysR2int mentioned in example 3 was electroporated by the electroporation method of Tauch et al. (FEMS Microbiological Letters, 123:343-347 (1994)) into *Corynebacterium glutamicum* DSM 5715 and *Brevibacterium lactofermentum* FERM BP-1763. The strain DSM 5715 is an AEC-resistant lysine producer (EP-B-435 132). The strain FERM BP-1763 is a valine producer in need of isoleucine and methionine (U.S. Pat. No. 5,188,948). The vector pCR2.1lysR2int cannot replicate independently in DSM 5715 or FERM BP-1763 and is retained in the cell only if it has integrated into the chromosome of DSM 5715 or FERM BP-1763. Selection of clones with pCR2.1lysR2int integrated into the chromosome was carried out by plating out the electroporation batch on LB agar (Sambrook et al., Molecular Cloning: A Laboratory Manual. $2^{nd}$ Ed., Cold Spring Harbor Laboratory Press, Cold Spring Harbor, N.Y.), which had been supplemented with 15 mg/l kanamycin.

For detection of the integration, the lysR2int fragment was labelled with the Dig hybridization kit from Boehringer by the method of "The DIG System Users Guide for Filter Hybridization" of Boehringer Mannheim GmbH (Mannheim, Germany, 1993). Chromosomal DNA of a potential integrant was isolated by the method of Eikmanns et al. (Microbiology 140: 1817-1828 (1994)) and in each case cleaved with the restriction enzymes SalI, SacI and HindIII. The fragments formed were separated by agarose gel electrophoresis and hybridized at 68° C. with the Dig hybrization [sic] kit from Boehringer. The plasmid pCR2.1lysR2int mentioned in example 3 had been inserted into the chromosome of DSM 5715 and FERM BP-1763 within the chromosomal lysR2 gene. The strains were called DSM5715:: pCR2.1lysR2int and FERM BP-1763:: pCR2.1lysR2int.

EXAMPLE 5

Preparation of L-Lysine and L-Valine

The *C. glutamicum* and *B. lactofermentum* strains DSM5715:: pCR2.1lysR2int and FERM BP-1763:: pCR2.1lysR2int obtained in example 4 were cultured in a nutrient medium suitable for the production of L-lysine and L-valine and the L-lysine and L-valine content in the culture supernatant was determined.

For this, the strains were first incubated on an agar plate with the corresponding antibiotic (brain-heart agar with kanamycin (25 mg/l) [sic] for 24 hours at 33° C. Starting from this agar plate culture, a preculture was seeded (10 ml medium in a 100 ml conical flask). The complete medium CgIII was used as the medium for the preculture.

| Medium Cg III | |
|---|---|
| NaCl | 2.5 g/l |
| Bacto-Peptone | 10 g/l |
| Bacto-Yeast extract | 10 g/l |
| Glucose (autoclaved separately) | 2% (w/v) |

The pH was brought to pH 7.4

Kanamycin (25 mg/l) was added to this. The preculture was incubated for 24 hours at 33° C. at 240 rpm on a shaking machine. A main culture was seeded from this preculture such that the initial OD (660 nm) of the main culture was 0.1 OD. Medium MM was used for the main culture.

| Medium MM | |
|---|---|
| CSL (corn steep liquor) | 5 g/l |
| MOPS | 20 g/l |
| Glucose (autoclaved separately) | 50 g/l |
| Salts: | |
| $(NH_4)_2SO_4$ [sic] | 25 g/l |
| $KH_2PO_4$ | 0.1 g/l |
| $MgSO_4 * 7H_2O$ | 1.0 g/l |
| $CaCl_2 * 2H_2O$ | 10 mg/l |
| $FeSO_4 * 7H_2O$ | 10 mg/l |
| $MnSO_4 * H_2O$ | 5.0 mg/l |
| Biotin (sterile-filtered) | 0.3 mg/l |
| Thiamine*HCl (sterile-filtered) | 0.2 mg/l |
| $CaCO_3$ | 25 g/l |

The CSL, MOPS and the salt solution are brought to pH 7 with aqueous ammonia and autoclaved. The sterile substrate and vitamin solutions are then added, as well as the $CaCO_3$ autoclaved in the dry state. For culturing of DSM 5715, 0.1 g/l leucine was additionally added to the medium. For culturing of FERM BP-1763, 0.1 g/l isoleucine and 0.1 g/l methionine were additionally added to the medium.

Culturing is carried out in a 10 ml volume in a 100 ml conical flask with baffles. Kanamycin (25 mg/l) was added. Culturing was carried out at 33° C. and 80% atmospheric humidity.

After 72 hours, the OD was determined at a measurement wavelength of 660 nm with a Biomek 1000 (Beckmann Instruments GmbH, Munich). The amount of L-lysine and of L-valine formed was determined with an amino acid analyzer from Eppendorf-BioTronik (Hamburg, Germany) by ion exchange chromatography and post-column derivatization with ninhydrin detection.

The results of the experiment are shown in tables 1 and 2.

TABLE 1

| Strain | OD(660) | Lysine HCl g/l |
|---|---|---|
| DSM5715 | 7.5 | 13.01 |
| DSM5715::pCR2.1lysR2int | 7.2 | 14.68 |

TABLE 2

| Strain | OD(660) | Valine g/l |
|---|---|---|
| FERM BP-1763 | 12.1 | 7.49 |
| FERM BP-1763::pCR2.1lysR2int | 13.4 | 10.90 | the abbreviations and designations used have the following meaning.

| | |
|---|---|
| KmR: | Kanamycin resistance gene |
| EcoRI: | Cleavage site of the restriction enzyme EcoRI |
| lysR2int: | Internal fragment of the lysR2 gene |
| ColEl ori: | Replication origin of the plasmid ColEl. |

The invention claimed is:

1. An isolated polynucleotide comprising:
   a fragment of SEQ ID NO: 1 that consists of at least 15 consecutive nucleotides, or
   a fragment of the full complement of SEQ ID NO: 1 that consists of at least 15 consecutive nucleotides.

2. The isolated polynucleotide of claim 1, wherein said fragment consists of at least 20 consecutive nucleotides of SEQ ID NO: 1.

3. The isolated polynucleotide of claim 1, wherein said fragment consists of at least 25 consecutive nucleotides of SEQ ID NO: 1.

4. The isolated polynucleotide of claim 1, wherein said fragment consists of at least 50 consecutive nucleotides of SEQ ID NO: 1.

5. The isolated polynucleotide of claim 2 which is bound to a solid support.

6. The isolated polynucleotide of claim 1, wherein said fragment consists of at least 15 consecutive nucleotides of the full complement of SEQ ID NO: 1.

7. The isolated polynucleotide of claim 1, wherein said fragment consists of at least 25 consecutive nucleotides of the full complement of SEQ ID NO: 1.

8. The isolated polynucleotide of claim 1, wherein said fragment consists of at least 50 consecutive nucleotides of the full complement of SEQ ID NO: 1.

9. The isolated polynucleotide of claim 6 which is bound to a solid support.

10. A hybridization probe or a PCR primer comprising the isolated polynucleotide of claim 1.

11. A method for detecting a polynucleotide which comprises contacting a nucleic acid sample with a hybridization probe or PCR primer comprising:
   a fragment of SEQ ID NO: 1 that consists of at least 15 consecutive nucleotides, or
   a fragment of the full complement of SEQ ID NO: 1 that consists of at least 15 consecutive nucleotides.

12. A method for producing a polynucleotide which comprises contacting a nucleic acid sample with at least one PCR primer comprising:
   a fragment of SEQ ID NO: 1 that consists of at least 15 consecutive nucleotides, or
   a fragment of the full complement of SEQ ID NO: 1 that consists of at least 15 consecutive nucleotides.

* * * * *